United States Patent
Auth et al.

[11] Patent Number: 6,030,380
[45] Date of Patent: Feb. 29, 2000

[54] RADIO FREQUENCY TRANSMYOCARDIAL REVASCULARIZATION

[75] Inventors: David C. Auth, Kirkland; Thomas J. Clement, Redmond, both of Wash.

[73] Assignee: BSC Northwest Technology Center, Inc., Redmond, Wash.

[21] Appl. No.: 08/884,058

[22] Filed: Jun. 27, 1997

Related U.S. Application Data

[60] Provisional application No. 60/032,805, Dec. 9, 1996.

[51] Int. Cl.$^7$ .................................................. A61B 17/30
[52] U.S. Cl. .............................. 606/41; 606/46; 607/101; 128/898
[58] Field of Search ................................ 128/898; 606/7, 606/13–16, 27, 28, 41, 45, 46, 49, 50; 607/119, 122; 600/374

[56] References Cited

U.S. PATENT DOCUMENTS

| | | | |
|---|---|---|---|
| 4,790,311 | 12/1988 | Ruiz | 128/303.1 |
| 4,896,671 | 1/1990 | Cunningham et al. | 128/642 |
| 5,047,026 | 9/1991 | Rydell | 606/48 |
| 5,093,877 | 3/1992 | Aita et al. | 385/34 |
| 5,358,485 | 10/1994 | Vance et al. | 604/22 |
| 5,364,393 | 11/1994 | Auth et al. | 606/34 |
| 5,370,675 | 12/1994 | Edwards et al. | 607/101 |
| 5,380,316 | 1/1995 | Aita et al. | 606/7 |
| 5,389,096 | 2/1995 | Aita et al. | 606/15 |
| 5,403,311 | 4/1995 | Abele et al. | 606/49 |
| 5,522,815 | 6/1996 | Durgin, Jr. et al. | 606/50 |
| 5,591,159 | 1/1997 | Taheri | 606/15 |
| 5,593,405 | 1/1997 | Osypka | 606/15 |
| 5,607,405 | 3/1997 | Decker et al. | 604/264 |
| 5,620,414 | 4/1997 | Campbell, Jr. | 604/22 |
| 5,672,174 | 9/1997 | Gough et al. | 606/41 |
| 5,681,308 | 10/1997 | Edwards et al. | 606/41 |
| 5,683,366 | 11/1997 | Eggers et al. | 604/114 |
| 5,697,882 | 12/1997 | Eggers et al. | 604/114 |
| 5,700,259 | 12/1997 | Negus et al. | 606/14 |
| 5,713,894 | 2/1998 | Murphy-Chutorian et al. | 606/15 |
| 5,725,521 | 3/1998 | Mueller | 606/7 |
| 5,725,523 | 3/1998 | Mueller | 606/15 |
| 5,755,714 | 5/1998 | Murphy-Chutorian | 606/15 |

FOREIGN PATENT DOCUMENTS

| | | |
|---|---|---|
| 296 09 350 U1 | 10/1996 | Germany. |
| 195 37 084 A1 | 4/1997 | Germany. |
| WO 96/35469 | 11/1996 | WIPO. |
| WO 96/39963 | 12/1996 | WIPO. |
| WO 97/18768 | 5/1997 | WIPO. |
| WO 97/29803 | 8/1997 | WIPO. |
| WO 97/32551 | 9/1997 | WIPO. |
| WO 97/44071 | 11/1997 | WIPO. |

OTHER PUBLICATIONS

M. L. Goldman et al., "Nonoperative Portacaval Shunt in Swine," *Investigative Radiology*, vol. 25, No. 5, May 1990, pp. 574–578.

(List continued on next page.)

*Primary Examiner*—Linda C. M. Dvorak
*Assistant Examiner*—David M. Ruddy
*Attorney, Agent, or Firm*—Crompton, Seager & Tufte, LLC

[57] ABSTRACT

An RF activated catheter apparatus for performing transmyocardial revascularization. The catheter apparatus including an elongate catheter shaft having proximal and distal ends, the distal end including an RF emitter which is coupled to an RF generator for cutting channels into the myocardium of a patient's heart.

3 Claims, 3 Drawing Sheets

OTHER PUBLICATIONS

Abstract entitled "Transventricular Revascularization by Laser", *Lasers in Surgery and Medicine*, 1982, 1 page.

Abstract entitled "Analysis of Photoproducts, Free Radicals and Particulate Debris Generated During In–Vivo Argon Laser Myoplasty", *Lasers in Surgery and Medicine*, 1991, 1 page.

Isner, J., "Right Ventricular Myocardial Infarction", *The Journal of the American Medical Association*, V259, N5, Feb. 5, 1988, 12 pages.

Abstract entitled "Proliferative Activity in Peripheral and Coronary Atherosclerotic Plaque . . . ", *J. Clin. Invest.*, Apr., 1993, 1 page.

A. Vineberg et al., "Creation of Intramyocardial Pathways to Channel Oxygenated Blood Between Ventricular Arteriolar Zones", *Canad. Med. Assoc. Journal*, Feb. 4, 1967, vol. 96, pp. 277–279.

A. Vineberg, M.D., "Results of 14 Years' Experience in the Surgical Treatment of Human Coronary Artery Insufficiency", *Canad. Med. Assoc. Journal*, Feb., 13, 1965, vol. 92, pp. 325–332.

A. Vineberg et al., "The Ivalon Sponge Procedure for Myocardial Revascularization", *Surgery*, vol. 47, No. 2, Feb., 1960, pp. 268–289.

A. Vineberg et al., "Investigative Surgery: Treatment of Acute Myocardial Infarction by Endocardial Resection", *Surgery*, vol. 57, No. 6, Jun., 1965, pp. 832–835.

P. Walter et al., "Treatment of Acute Myocardial Infarction by Transmural Blood Supply From the Ventricular Cavity", *Europ. Surg. Res.*, 3:130–138 (1971).

H.A. Khazei et al., "Myocardial Canalization: New Method of Myocardial Revascularization", *The Annals of Thoracic Surgery*, vol. 6, No. 2, Aug., 1968, pp. 163–171.

J. Hershey et al., "Transmyocardial Puncture Revascularization: a Possible Emergency Adjunct to Arterial Implant Surgery", *Geriatrics*, Mar., 1969, pp. 101–108.

Press Release dated Oct. 21, 1996, entitled "Doctors Demonstrate Proof of Blood Flow Through Open TMR Channels Created with PLC Systems . . . ", PLC Systems, Inc., 1 page.

Press Release dated Oct. 10, 1996, entitled "Texas Fieart Institute Presents Study Comparing the Use of CO2, Holmrum and Excimer Lasers for TMR", 1 page.

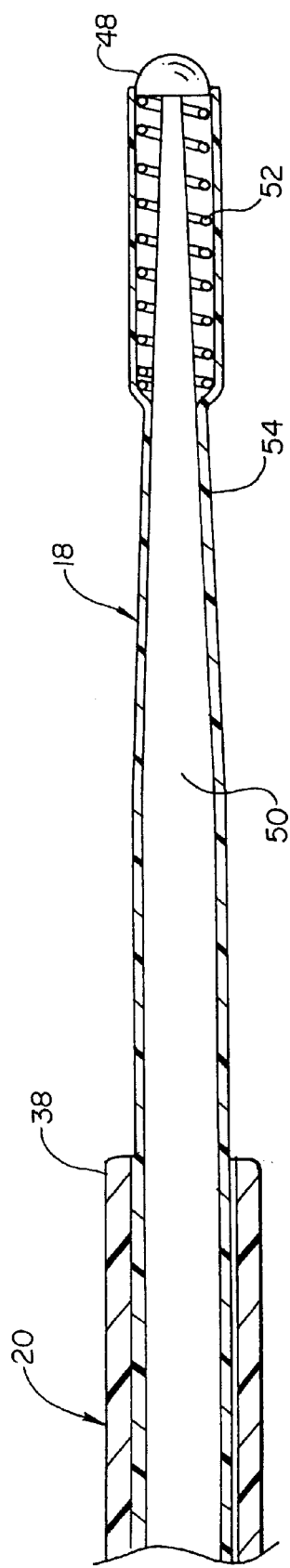
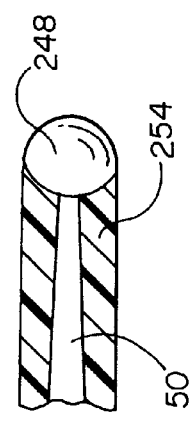
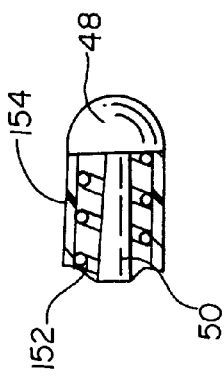
Fig. 3
Fig. 5
Fig. 4

RADIO FREQUENCY TRANSMYOCARDIAL REVASCULARIZATION

RELATED CASES

This application claims the benefit of U.S. Provisional Application No. 60/032,805, filed Dec. 9, 1996. The present application is related to U.S. patent application Ser. No. 08/792,094, filed Jan. 31, 1997, entitled "Radio Frequency Transmyocardial Revascularization Corer", and is incorporated herein by reference.

FIELD OF THE INVENTION

The present invention pertains to a device and method for performing transmyocardial revascularization (TMR) using radio frequency (RF) energy.

BACKGROUND OF THE INVENTION

A number of techniques are available for treating cardiovascular disease such as cardiovascular bypass surgery, coronary angioplasty, laser angioplasty and atherectomy. These techniques are generally applied to bypass or open lesions in coronary vessels to restore or increase blood flow to the heart muscle. In some patients, the number of lesions is so great, or the location so remote in the patient's vasculature, that restoring adequate blood flow to the heart muscle is difficult.

TMR has been developed as an alternative to these techniques which are directed at bypassing or removing lesions. TMR is performed by boring channels directly into the myocardium of the heart. In one such procedure, a laser catheter is advanced into the left ventricle. Laser radiation is then focused on the myocardium to create a channel. It has been found that creating several channels may be useful.

TMR has been performed by forming channels with laser energy as described above. TMR has also been performed by cutting a channel with a sharpened probe or blade. The channels cut by laser have a width proportional to the width of the focused laser radiation used to make the channels. When a laser is used, tissue is vaporized to form the channel. When the procedure is performed with a blade, tissue is not removed, but merely pierced or cut.

Lasers used to perform TMR can be costly and the depth of the channels formed can be difficult to control. Removing, or in the case of the TMR laser techniques, vaporization of tissue is believed to enhance the success of the TMR procedure.

SUMMARY OF THE INVENTION

The present invention pertains to an apparatus and method for performing TMR using RF energy. The apparatus and method of the present invention provides a means for performing TMR by creating channels in the myocardium of the patient's heart which can vary in length and width. The depth of the channels is generally believed to be directly proportional to the distance which the catheter of the present invention is advanced into the patient's myocardium. This method of forming the channels can be referred to as spark erosion.

Two theories underlie this procedure. The leading theory holds that creation of the channels causes angiogenesis as a healing response. When angiogenesis occurs, additional blood vessels grow in the myocardium near the channels. The second theory of TMR is that the creation of channels provides direct access of pooled blood in the heart to the heart muscle.

In one embodiment of the present invention, the RF activated catheter apparatus includes an elongate metallic member. The metallic member has a proximal end and a distal end. The distal end can be tapered in a distal direction. An RF generator is coupled to the metallic member proximate its proximal end.

Preferably, an insulator surrounds a portion of the distal end of the metallic member. This insulator could be, for example, polytetrafluoroethylene (PTFE) to reinforce the tapered portion of the elongate metallic member, a helical coil can be disposed between the metallic member and the insulator.

When using the catheter apparatus of the present invention to perform TMR, the distal end of the catheter apparatus is advanced to the patient's heart, the hibernating tissue to be cut having previously been identified by techniques such as angiography. The RF generator is activated to deliver RF energy to the distal end to begin boring a channel into the myocardium of the patient's heart. The depth of the channel is preferably greater than its width. A guide catheter, steerable tip catheter, deflectable tip catheter or the like may be used while advancing the distal end of the catheter apparatus.

BRIEF DESCRIPTION OF THE DRAWINGS

FIG. 3 is a cross sectional view of the distal end of the catheter apparatus of FIG. 2;

FIG. 4 is a cross sectional view of an alternate embodiment of a distal end of the catheter apparatus of FIG. 2; and FIG. 5 is a cross sectional view of yet another alternate embodiment of the distal end of the catheter apparatus of FIG. 2.

DETAILED DESCRIPTION OF THE INVENTION

Figure 1:
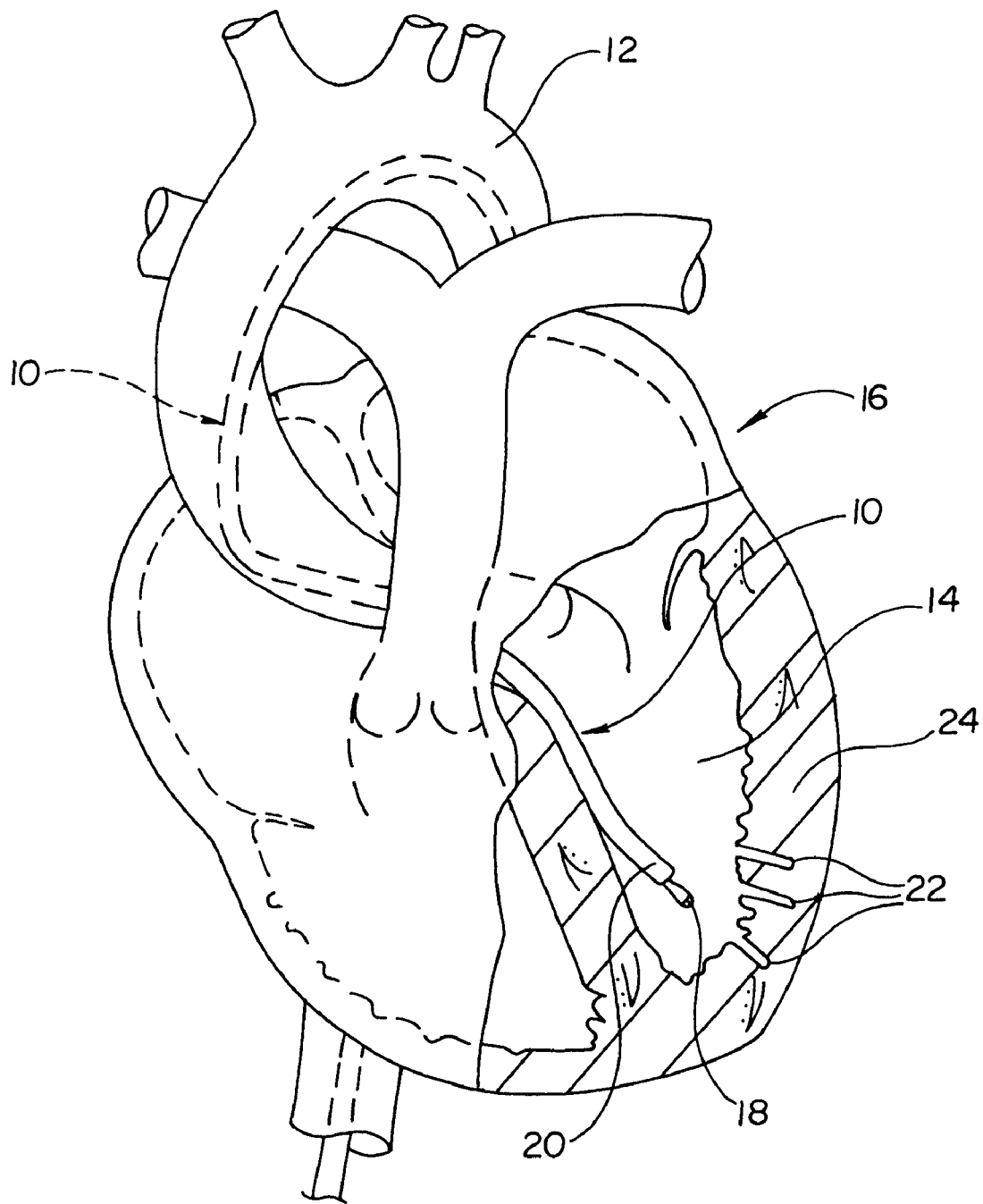
FIG. 1 is a cut-away view of a human heart including an RF transmyocardial revascularization catheter apparatus in accordance with the present invention.

Referring now to the drawings wherein like reference numerals represent like elements throughout the several views, FIG. 1 is a view of a portion of an radio frequency transmyocardial revascularization (RF TMR) catheter assembly 10 disposed within an aorta 12 and a left ventricle 14 of a heart 16. The elements of catheter assembly shown in FIG. 1 include an RF activated catheter 18, partially extending from a tubular catheter 20. Catheter 20 can be a guide catheter for advancing RF activated catheter 18 therethrough or to shield portions of a patient's anatomy from RF energy emitted from catheter 18. Three channels 22 cut by catheter 18 are shown in myocardium 24 of heart 16. As a consequence of creating these channels by performing the TMR procedure, it is believed that revascularization of the myocardium near the channels occurs by angiogenesis, or the channels themselves provide access by pooled blood from ventricle 14 to myocardial tissue.

Figure 2:
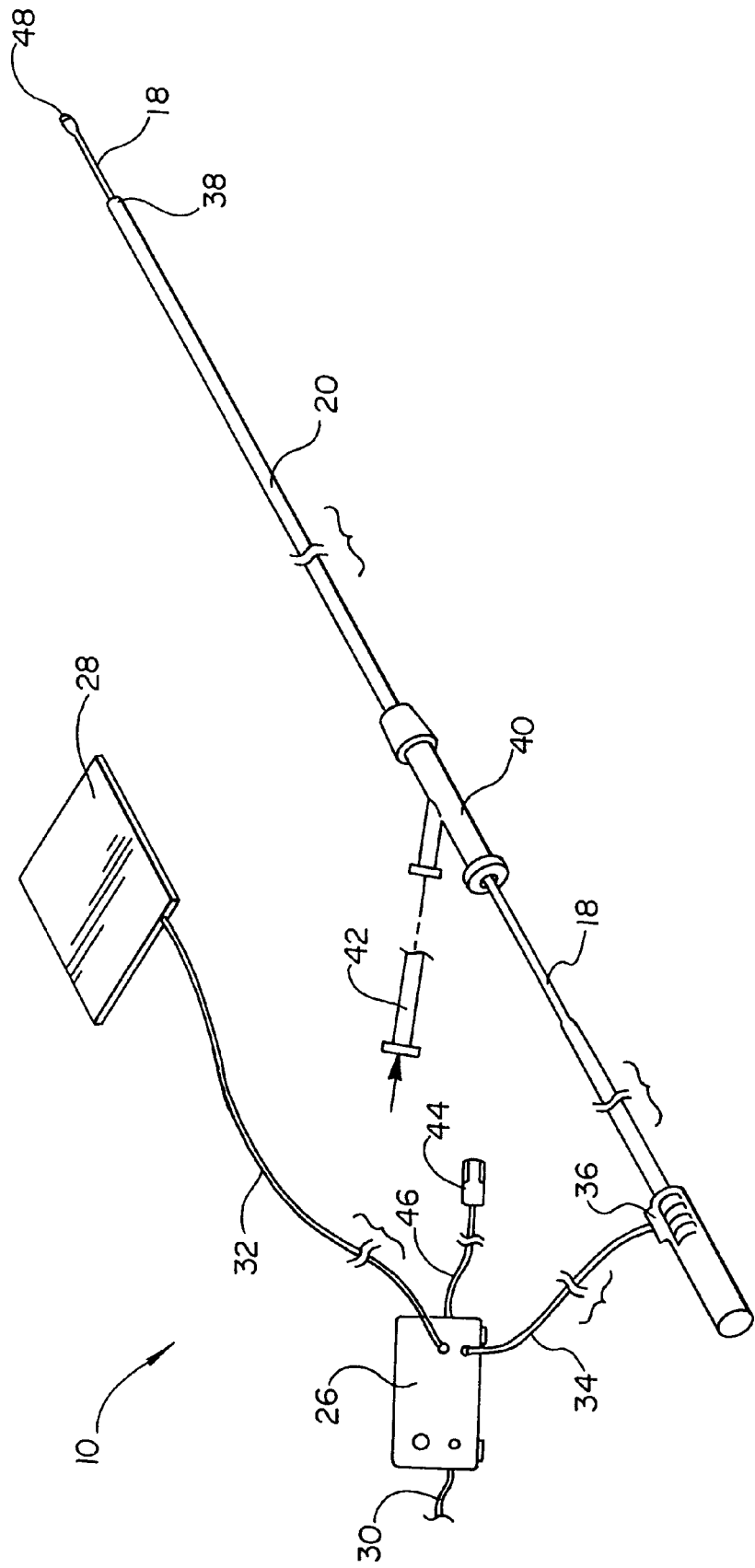
FIG. 2 is a diagram of the RF transmyocardial revascularization assembly including RF generator ground plane and catheter.

FIG. 2 is a view of RF TMR catheter assembly 10 including RF activated catheter 18, an RF generator 26 and a ground plate 28. Alternatively, ground plate 28 need not be used as the intrinsic body capacitance of the patient can complete the circuit. RF generator 26 is connected to a power source by a cable 30. A cable 32 connects a ground plate 28 to RF generator 26. Catheter 18 is connected to generator 26 at a handle 36 at the proximal end of catheter 18 by a cable 34. The RF output from generator 26 is preferably isolated from 60 Hz ground to avoid low frequency electrical shock hazard to the patient.

Catheter 20 is preferably a flexible catheter, such as a guide catheter having an atraumatic distal tip 38 and a Yadaptor 40 at its proximal end. Catheter 20 can also be a steerable tip catheter, deflectable tip catheter or the like. Y-adaptor 40 preferably includes a side arm 42 which can be used to perfuse saline or contrast media through catheter 20 to distal tip 38.

A foot pedal 44 can be connected to RF generator 26 to control the delivery of RF energy to a distal ablating tip 48 of RF activated catheter 18. A prior RF activated catheter developed by Auth et al. is disclosed by U.S. Pat. No. 5,364,393 which issued Nov. 15, 1994 and is incorporated herein by reference.

FIG. 3 is a cross sectional view of the distal ends of catheters 18 and 20. Catheter 18 preferably includes an elongated metallic core member 50. The distal end of core member 50 can be tapered distally to enhance the steerability of catheter 18. A portion of the tapered section can be surrounded by a coil 52 to enhance flexibility of catheter 18. Distal cutting tip 48 preferably is a hemispherical or spherical metallic member. Tip 48, core member 50 and coil 52 can be formed from stainless steel or other biocompatible materials such as nitinol. In one embodiment, coil 52 can be formed from a radiopaque material such as platinum. An insulative sheath 54 is preferably disposed over core member 50 and coil 52 to focus the emission of RF energy through tip 48 in a generally distal direction. Insulation sheath 54 can be extended distally to enhance the focusing of the RF energy in a substantially distal direction to eliminate any clinically significant transverse component. Insulative sheath 54 can be formed from polytetraf luoroethylene (PTFE) or other biocompatible insulative material.

FIG. 4 is a cross sectional view of an alternate embodiment of the distal end of the RF catheter in accordance with the present invention. This embodiment is similar to that shown in FIG. 3 except that this alternate embodiment includes a coil 152 having a reduced diameter such that an insulation sheath 154 can abut generally hemispherically shaped tip 48 without extending transversely beyond the periphery of tip 48.

FIG. 5 is a cross sectional view of yet another distal end of an RF catheter in accordance with the present invention. Unlike the distal end shown in FIGS. 3 and 4, the end shown in FIG. 5 includes an insulation sheath 254 which surrounds core member 50 without the interposition of a coil. Insulation sheath 254 is shown extending distally to surround a distal tip 248 at approximately its maximum transverse extent. Coil 152, insulating sheaths 154 and 254 and tip 248 can be formed from materials like those used to form the corresponding elements in the embodiments shown in FIG. 3.

In use, distal ablating tip 48 of RF TMR catheter assembly 10 is advanced to a patient's heart, the hibernating tissue to be cut having previously been identified by means known to those skilled in the art, such as angiography. Typically, hibernating tissue can be identified by injecting contrast media into coronary vessels to identify regions of the heart into which the contrast medium does not flow due to obstruction of the vessels into which the media is injected. In this case, the hibernating region will be identified by the lack of flow or abnormally low flow distally of the obstruction in the coronary vessel or vessels. Alternatively, the contrast media can be injected directly into the heart chambers to identify areas within the chamber which have generally stagnant, pooled blood. If contrast media has been injected into the coronary vessels, those regions of the heart into which the contrast media does not flow, would be candidates for the RF TMR procedure. If contrast media is injected directly into the heart chambers, the regions of the heart adjacent to the generally stagnant pooled blood would be candidates for the RF TMR procedure.

Access to the patient's heart can be established percutaneously by way of aorta 12 and left ventricle 14. Alternatively, access can be obtained by way of aorta 12 and a coronary artery (not shown). RF generator 26 is activated to deliver RF energy to tip 48. To create the channels, tip 48 is brought into contact with the wall of the patient's heart and advanced into the myocardium a predetermined depth or to a depth determined intraprocedurally based on measurements taken from an imaging system (e.g., fluoroscopy) in order to form a channel. This process can be repeated to form additional channels in the patient's myocardium. The depth of each channel and the number of channels depend upon the objectives of the particular TMR treatment. The depth of the channels can be nearly as great as the thickness of the heart wall, for example, approximately 2 cm, but the channel should not extend entirely through or puncture the heart wall.

The length of each channel is preferably greater than their width. To aid in creating this geometry, the insulative sheath 54 can be extended as described above to focus RF energy distally to reduce any transverse component. The width of tip 48 can be varied to generally proportionally vary the width of the channels. Tip 48 can be greater in diameter then the diameter of core member 50. In one embodiment, the diameter of tip 48 measured perpendicularly to the length of catheter 18 is approximately 2 mm. The tissue damage adherent to the channel, can be varied by varying the modulation envelope or power of the RF waveform. For example, increasing the crest-factor or ratio of peak to RMS voltage would increase the tissue damage adherent to the channel. This may increase angiogenesis associated with the formation of each channel.

RF activated catheter 18 can be advanced to the patient's heart through tubular catheter 20. Saline solution or contrast medium can be delivered to distal tip 38 of catheter 20.

Foot pedal 44 can be used to pulse the delivery of RF energy to distal ablating tip 48. In a preferred embodiment, the power output of the RF radiation can be operator selected and controlled by RF generator 26. Varying the pulse duration will vary the cutting rate, or penetration depth per pulse applied, of distal tip 48. For example, increasing the pulse duration will increase the cutting rate at a given power level. The power level can also be increased to increase cutting rate.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts or waveforms without exceeding the scope of the invention. The inventions's scope is, of course, defined in the language in which the appended claims are expressed.

What is claimed is:

1. A method of performing transmyocardial revascularization comprising the steps of:

providing a radio frequency catheter apparatus including an elongate shaft having a proximal end and a distal end;

the radio frequency catheter being coupled to a radio frequency generator;

advancing the distal end of the catheter to a patient's heart;

perfusing a contrast media through the radio frequency catheter to the patients heart;

identifying an area of the patient's heart which is adjacent to a stagnant pool of the contrast media thereby diagnosing the location of a candidate region of the patient's heart;

further advancing the distal end of the catheter to the candidate region of the patient's heart; and activating the radio frequency generator to deliver radio frequency energy to the distal end of the radio frequency catheter to begin boring a crater into the patient's heart.

2. A method of performing transmyocardial revascularization, comprising the steps of:

providing a radio frequency catheter apparatus including an elongate shaft having a proximal portion, a distal tip, and a lumen extending longitudinally therethrough;

the radio frequency catheter being coupled to a radio frequency generator;

advancing the distal tip of the catheter to a patient's heart;

perfusing a contrast media through the radio frequency catheter to the distal tip of the radio frequency catheter thereby delivering the contrast media to the patient's heart;

further advancing the distal tip of the catheter to an area of the patient's heart adjacent to a stagnant pool of the contrast media; and activating the radio frequency generator to deliver radio frequency energy to the distal tip of the radio frequency catheter to begin boring a crater into the patient's heart.

3. A method of performing transmyocardial revascularization, comprising the steps of:

providing a radio frequency catheter apparatus including an elongate shaft having a proximal portion, a distal tip, and a lumen extending longitudinally therethrough;

the proximal portion of the radio frequency catheter including a Y-adapter having a side arm containing a contrast media;

the radio frequency catheter being coupled to a radio frequency generator;

advancing the distal tip of the catheter to a patient's heart;

perfusing the contrast media contained in the side arm through the radio frequency catheter to the distal tip of the radio frequency catheter thereby delivering the contrast media to the patient's heart;

further advancing the distal tip of the catheter to an area of the patient's heart adjacent to a stagnant pool of the contrast media; and activating the radio frequency generator to deliver radio frequency energy to the distal tip of the radio frequency catheter to begin boring a crater into the patient's heart.

* * * * *